United States Patent [19]

Kennedy et al.

[11] Patent Number: 5,338,547
[45] Date of Patent: Aug. 16, 1994

[54] BOWMAN-BIRK INHIBITOR PRODUCT FOR USE AS AN ANTICARCINOGENESIS AGENT

[75] Inventors: Ann R. Kennedy, Wynnewood, Pa.; Bernard F. Szuhaj, Fort Wayne, Ind.

[73] Assignees: Trustees of the Univ. of Pennsylvania, Philadelphia, Pa.; Central Soya, Fort Wayne, Ind.

[21] Appl. No.: 973,335

[22] Filed: Nov. 2, 1992

Related U.S. Application Data

[63] Continuation-in-part of Ser. No. 824,719, Jan. 17, 1992, Pat. No. 5,217,717, which is a continuation-in-part of Ser. No. 579,155, Sep. 6, 1990, abandoned.

[51] Int. Cl.$^5$ .................... A61K 35/78; A61K 47/00
[52] U.S. Cl. ................... 424/195.1; 514/783
[58] Field of Search ................ 424/195.1; 514/783

[56] References Cited

U.S. PATENT DOCUMENTS 3,365,440  1/1968  Circle et al. ............... 260/123.5
4,793,996  12/1988  Kennedy et al. ............ 424/195.1

OTHER PUBLICATIONS

Baturay et al., *Cell Biology and Toxicology* 1986, 2, 21–32.
Berenblum et al., *Radiat. Res.* 1974, 60, 501–505.
Billings et al., *Carcinogenesis* 1990, 11, 1083–1086.
Bowman, *Proc. Soc. Exptl. Med.* 1946, 63, 547–550.
Birk et al., *Bull. Res. Council Israel* 1962, Sec. A 11, 48.
Birk, *Biochim. Biophys. Acta* 1963, 67, 326–328.
Hwang et al., *Biochem. Biophy. Acta.* 1977, 495, 369–382.
*Methods Enzymol* 1970, 19, 860–862.
Kennedy et al., *Proc. Nat'l. Acad. Sci. USA* 1984, 81, 1827–1839.
Kennedy et al., *Anticarcinogenesis and Radiation Protection,* Cerutti et al., Eds., Plenum Pub, 1987, pp. 285–295.
Kennedy, A. R. *Mechanisms of Tumor Promotion* vol. III, T. J. Slaga, Eds., CRC Press, 1984, Chapter 2, pp. 13–55.
Messadi et al., *J. Natl. Cancer Inst.* 1986, 76, 447–452.
Morris, *J. Dent. Res.* 1961, 40, 3–15.
M. Naim et al., *Br. J. Nutr.* 1982, 47, 281–288.
Odani and Ikenaka, *J. Biochem.* 1973, 74, 857.
Perlmann et al., *Methods in Enzymology* 1970, 19, 860–862.
Salley, *J. Dent. Res.* 1954, 33, 253–262.
St. Clair et al., *Cancer Res.* 1990, 50, 580–586.
von Hofe et al., *Carcinogenesis* 1991, 12, 2147–2150.
Weed et al., *Carcinogenesis* 1985, 6, 1239–1241.
Witschi et al., *Carcinogenesis* 1989, 10, 2275–2277.
Yavelow et al., *Proc. Natl. Acad. Sci. USA* 1985, 82, 5395–5399.

*Primary Examiner*—John W. Rollins
*Attorney, Agent, or Firm*—Jane Massey Licata

[57] ABSTRACT

Methods for the suppression and inhibition of carcinogenesis are provided in which a Bowman-Birk product produced in accordance with the processes described are administered. The methods are particularly adaptable to the prevention or treatment of colon, lung, liver, esophagus, oral epithelium (squamous carcinomas), and bone marrow cancer. The preferred mode of administration is as a dietary supplement.

18 Claims, 3 Drawing Sheets

Number of Tumors Observed in the Various Treatment Groups
(Histogram Form of Data Presented in Table I)

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
 ( A ) LENGTH: 4
 ( B ) TYPE: amino acid
 ( D ) TOPOLOGY: linear ( x i ) SEQUENCE DESCRIPTION: SEQ ID NO: 1:

Ala Ala Pro Phe
4

BOWMAN-BIRK INHIBITOR PRODUCT FOR USE AS AN ANTICARCINOGENESIS AGENT

INTRODUCTION

The invention described herein was made in the course of research supported in part by the National Institutes of Health under grant numbers NIH 5-R37-CA 22704-13; NIH 7-R01-CA 34680-07; and NIH 7-U01-CA 46496-02. The government may have certain rights in this invention.

This application is a continuation-in-part of Ser. No. 824,719 filed Jan. 17, 1992, now U.S. Pat. No. 5,217,717, which is a continuation of Ser. No. 579,155, filed Sep. 6, 1990, now abandoned.

FIELD OF THE INVENTION

This invention relates to a unique preparation of a novel Bowman-Birk Inhibitor concentrate (BBIC) from the soybean. BBIC has been shown to exhibit inhibitory activity against the malignant transformation of cells under certain conditions and its administration shown to affect various forms of carcinogenesis.

BACKGROUND OF THE INVENTION

It has been shown that the enzyme-inhibitor described by Bowman, *Proc. Soc. Exptl. Med.* 1946, 63, 547, and Birk et al., *Bull. Res. Council Israel* 1962, Sec. A 11, 48 and *Biochim. Biophys. Acta* 1963, 67, 326, and subsequently referred to as the Bowman-Birk Inhibitor (BBI), possesses certain physiological activity that prevents, or at least greatly reduces, radiologically or chemically induced malignant transformation of cells in culture and in experimental animals.

Yavelow et al., *Proc. Natl. Acad. Sci. USA* 1985, 82, 5395–5399, reported that a crude soybean extract, if defatted with acetone, effectively blocked cell transformation in vitro. An active component of this crude extract is the BBI. These observations, with epidemiological data, suggested BBI as a putative dietary anticarcinogen, particularly with respect to colon cancer.

Weed et al., *Carcinogenesis* 1985, 6,1239–1241, disclose that an extract of soybeans containing the Bowman-Birk protease inhibitor added to the diet of dimethylhydrazine (DMH)-treated mice resulted in a significant suppression of odenomatous tumors of the colonic mucosa. Weed et al. noted that DMH-induced colon cancer in mice is generally regarded as an excellent animal model for the human disease, with carcinogen treatment inducing adenocarcinomas of the colon and rectum which are similar to the tumors arising in the human colon. The Weed et al. study suggested the possibility that a dietary additive of the sort studied might confer some protection against the development of human colon cancer without undesirable side effects. The BBI extract and methods for its preparation were as described by Yavelow et al., *Proc. Natl. Acad. Sci. USA* 1985, 82, 5395–5399.

Messadi et al., *JNCI* 1986, 76,447–452, demonstrated that a soybean extract containing the protease inhibitor BBI suppresses 7,12-dimethyl-benz[a]anthracene (DMBA)-induced carcinogenesis in the hamster cheek pouch. This oral cancer model, with the use of the hamster check pouch carcinogenesis system, has the same histopathology, growth pattern, and precancerous lesions as the most common form of human oral cancer, squamous cell carcinoma. It was shown in this study that hamster cheek pouch carcinogenesis can be inhibited by BBI and suggested that human oral carcinogenesis might respond to BBI in a comparable manner. The BBI preparation used in this study was a crude extract of the inhibitor prepared as described by Yavelow et al., supra.

Baturay et al., *Cell Biology and Toxicology* 1986, 2, 21–32, disclose that a BBI preparation, wherein a crude soybean extract is defatted with acetone, suppresses radiation and chemically induced transformation in vitro, with or without enhancement by the co-carcinogen, pyrene. Yavelow et al., supra, show that either pure BBI or the BBI extract prepared in accordance with their methods suppresses radiation induced transformation in C3H10T1/2 cells. Kennedy et al., *Proc. Nat'l. Acad. Sci. USA* 1984, 81, 1827–39, report that either pure BBI or the BBI extract prepared in accordance with their method reduce the levels of chromosome abnormalities in cells of patients with Bloom's syndrome (a genetic disease in which the high levels of chromosome abnormalities are thought to predispose the patients to a higher than normal cancer incidence). Still, other studies suggest that soybean-derived protease inhibitors can have suppressive effects on skin, breast and liver carcinogenesis in vivo.

Kennedy et al., *Anticarcinogenesis and Radiation Protection*, Cerutti et al., Eds., Plenum Pub, 1987, pp. 285–295, disclose that BBI suppresses carcinogenesis in various systems using a crude BBI extract prepared by defatting soybeans with acetone. Their results suggested that very low concentrations of BBI-type protease inhibitor preparations would be effective as chemopreventative agents for colon cancer. There was no evidence to suggest that the use of protease inhibitors as chemopreventative agents would be complicated by possible toxicity problems.

St. Clair et al., *Cancer Res.* 1990, 50,580–586 report that the addition of 0.5% or 0.1% semi-purified BBI or 0.1% or 0.01% purified BBI to the diet of DMH-treated mice resulted in a statistically significant suppression of angiosarcomas and nodular hyperplasia of the liver and colon carcinogenesis. The results of this study also indicate that BBI, included as 0.5% of the diet or less had no adverse effect upon the health of the mice but had the capacity to suppress liver and colon carcinogenesis.

The use of a BBI product was shown to modify the development of lung tumors induced chemically by intraperitoneal (i.p.) injection of 3-methylcholanthrene (MCA) in male strain A mice. Witschi et al., *Carcinogenesis* 1989, 10, 2275–2277. BBI products have been shown to act as chemopreventative agents to suppress the development of esophageal carcinogenesis induced by i.p. injection of N-nitrosomethylbenzylamine (NMBzA) in male rats. von Hofe et al., *Carcinogenesis* 1991, 12, 2147–2150. It has also been shown that BBI products effectively reduce the incidence of dimethylhydrazine-induced adenocarcinomas of the colon of mice. Billings et al., *Carcinogenesis* 1990, 11, 1083–1086.

Various processes have been disclosed for the preparation of different forms of BBI products. Perlmann et al., *Methods in Enzymology* 1970, 19,860–861, have described an elaborate method for obtaining a BBI product from a defatted soybean extract using an ethanol extraction step.

U.S. Pat. No. 4,793,996 (Kennedy et al.) discloses a process comprising treating soybeans with acetone, followed by ethanol extraction and acetone precipitation for obtaining BBI. The soybeans may be defatted prior to acetone treatment. In addition, BBI may be further purified by conventional techniques. Kennedy et al. discovered that in the conventional process for preparing BBI from soybeans, a factor remained which adversely affected the ability of BBI to inhibit the malignant transformation of cells. If the factor was removed, the resulting BBI product was capable of inhibiting the malignant transformation of cells. It was found to be possible to remove this factor by treating the soybeans with acetone prior to the ethanol extraction step used by Perlmann et al.

Kennedy et al. teach that it is unnecessary to carry out a procedure requiring complete purification of the extract to the point where the product contains only a single protein, but instead it has been found effective to stop the purification procedure at a point where a crude inhibitor extract is obtained. This crude extract (i.e., concentrate) is itself edible and can be used as an inhibitor of malignant transformation of cells, for example by oral ingestion. Kennedy et al. disclose a process for preparing a crude soybean extract containing an inhibitor of malignant cell transformation which comprises defatting soybeans and extracting said inhibitor from said defatted soybeans; the improvement comprises defatting said soybeans by bringing them into contact with at least an equal weight of acetone and, thus, producing a crude inhibitor extract having greatly increased effectiveness.

Kennedy et al., in U.S. Pat. No. 5,217,717 entitled "Methods of Making Soybean Bowman-Birk Inhibitor Concentrate and Use of Same As a Human Cancer Preventative and Therapy", which is incorporated herein in its entirety, describes the methods for producing novel BBI concentrate products. Those BBI concentrate products are employed by the methods of the present invention. The process described to produce those BBI products was found to be economically superior due to the avoidance of an aqueous alcohol extraction step and the use, in certain embodiments, of ultrafiltration as a separation process step.

SUMMARY OF THE INVENTION

The methods of the present invention provide for the use of novel Bowman-Birk inhibitor concentrate (BBIC) products, produced in accordance with the processes described herein, for the suppression or inhibition of carcinogenesis. Carcinogenesis, as defined herein, is the process of the malignant transformation of cells from normal cells to cancer cells. This term encompasses both the inception of cancer cell production and also the progression of cancer cell development to include the extension and metastasis of cancer cells to other sites, such as other organ sites. While the use of the methods of the present invention employing the BBIC products described herein has been shown to suppress or inhibit the inception of some forms of carcinogenesis, the use of the same methods to produce BBIC and autoclaved BBIC products has been shown to suppress or inhibit extension and metastasis.

The methods described by the present invention employ the use of an effective amount of a BBIC product having a high level of biological activity as measured by chymotrypsin inhibitor (CI) content and/or the ability to suppress or inhibit radiologically or chemically induced malignant transformation of cells. The source material for preparing the BBIC products is soybean solubles. The soybean solubles are preferably obtained from soybean flakes or soy flour. The soybean flakes or soy flour are first subjected to a hexane defatting step. The defatted material is subjected to an acidic aqueous extraction step, pH from about 4 to 5, and the insolubles are removed to produce the soybean solubles. The process for the production of soybean solubles are well known in the art as shown by U.S. Pat. No. 3,365,440, which is incorporated herein in its entirety. The soybean solubles are conventionally produced at a relatively high solids concentration, usually at a solids concentration of at least about 50 percent by weight as recognized by the Association of American Feed Control Officials Incorporated.

The BBIC product is produced by diluting the soybean solubles with water, preferably to about 15–25% by weight solids content, followed by centrifugation to produce purified soybean solubles. The purified solubles are then diluted with water, preferably to about 10–12% by weight solids, to produce reslurried purified soybean solubles. The reslurried solubles are then subjected to ultrafiltration to produce a crude BBI concentrate. The crude concentrate is then diluted with water and spray dried to produce the BBIC product. In another process embodiment for the production of the BBIC product, the diluted crude BBI concentrate is subjected to another ultrafiltration step to produce a semi-crude BBI concentrate which is then spray dried to produce the BBIC product.

In a preferred process embodiment, the semi-crude BBI concentrate is treated with acetone to produce a BBI concentrate precipitate. After settling and decanting the resulting purified BBI concentrate precipitate is air dried, ground, reslurried with water, filtered and then lyophilized or spray dried to produce the BBIC product.

The BBIC product can be produced in accordance with another process embodiment wherein the time-consuming ultrafiltration step(s) are eliminated by starting with soy solubles and applying the acetone treatment to a substrate that has a substantially higher concentration of BBI than that in the defatted soy flour/flake of the prior art, resulting in a more economical process for production.

It was surprisingly found that the BBIC products produced in accordance with the processes set forth herein are significantly improved inhibitors of malignant cell transformation over prior art BBI products.

DETAILED DESCRIPTION OF THE INVENTION

Figure 1:
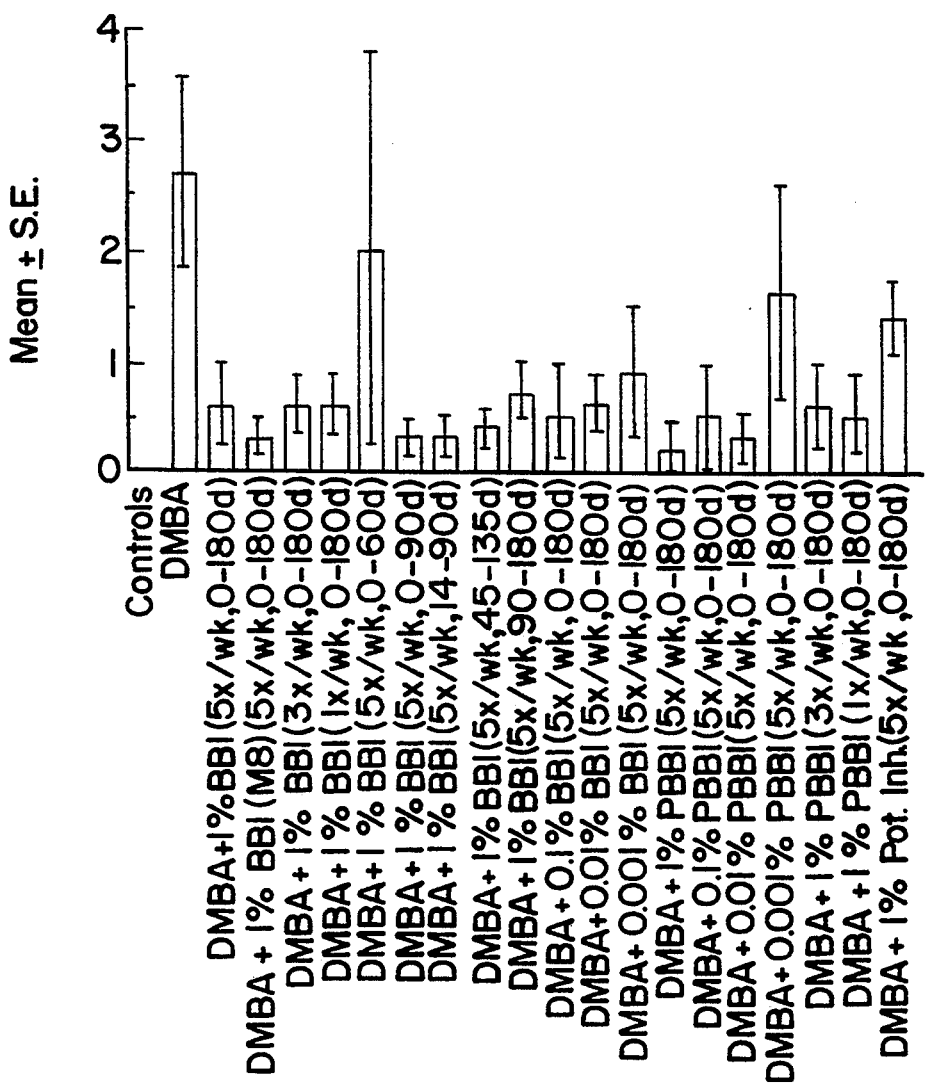
FIG. 1 is a histogram showing the number of tumors observed in the animal study treatment groups and showing the usefulness of the BBIC product produced by the processes set forth herein in inhibiting carcinogenesis.

The present invention concerns improved methods of inhibiting or suppressing carcinogenesis by the administration of novel Bowman-Birk inhibitor concentrate (BBIC) products. The BBIC products are produced by the methods described herein. The administration can be by any acceptable and convenient mode, and oral administration is preferred for most applications.

The preparation of the BBIC product used in the methods of the present invention includes the steps of (1) providing soybean solubles produced from acidic aqueous-extracted hexane-defatted soybeans in the absence of an ethanol extraction step, the soybean solubles preferably having a solids concentration of at least about 50 percent by weight; (2) diluting the soybean solubles with an aqueous solution to form a slurry, preferably a 15 to 20 percent by weight solid solution; (3) separating the aqueous soluble portion of the soybean solubles from the slurry to form a purified soybean soluble composition; (4) diluting the purified soybean soluble composition with an aqueous solution, preferably to about a 10–12% solid solution, and ultrafiltering the aqueous soluble portion of the diluted purified soybean soluble composition at least once, retaining the supernatant fluid, to form a crude BBI concentrate; and (5) drying the crude BBI concentrate, preferably by spray drying, and recovering the BBIC product. The process can include an optional, additional dilution of the crude BBI concentrate with an aqueous solution followed by an ultrafiltration step to form a semi-crude BBI concentrate prior to the drying step. The process can be further modified by diluting the semi-crude BBI concentrate with acetone and retaining the precipitated acetone insoluble portion prior to the drying step.

In accordance with one embodiment of the process to produce the BBIC product, soybean solubles are diluted with water to 18% solids and then centrifuged to produce purified soybean solubles. The purified solubles are diluted with water to 8% solids to produce reslurried purified soybean solubles which are subjected to ultrafiltration (1,000 m.w. membrane). The resulting crude BBI concentrate is diluted with water (1:1) and then subjected to a second ultrafiltration step (1,000 m.w. membrane) to produce a semi-crude BBI concentrate. The semi-crude concentrate is treated with acetone (2.2:1) to produce a BBI concentrate precipitate. After settling and decanting, the resulting purified BBI concentrate precipitate is air dried, ground, reslurried with water to 15% solids, filtered (Buchner funnel/Whatman #1) and then lyophilized to produce the BBIC product.

In another embodiment of the process to produce the BBIC product, purified soybean solubles are produced as described above and then diluted to 10% solids. The resulting reslurried purified soybean solubles are then treated as described in the foregoing to produce a semi-crude BBI concentrate which is treated with acetone (1.66 to 1) to produce a BBI concentrate precipitate. The BBIC product is produced as described above, with the exception that the filtered precipitate is spray dried rather than lyophilized.

In still another embodiment of the process to produce the BBIC product, soybean solubles are diluted with water to 15–20% solids and centrifuged to produce purified soybean solubles. The purified solubles are diluted with water to 10% solids to produce reslurried purified soybean solubles which are subjected to ultrafiltration (1,000 m.w. membrane). The resulting crude BBI concentrate is diluted with water (1:1) and spray dried to produce the BBIC product.

In yet another embodiment of the process to produce the BBIC product, soybean solubles are diluted with water to 16% solids and centrifuged to produce purified soybean solubles. The purified solubles are diluted with water to 10% solids. The resulting reslurried purified solubles are then subjected to ultrafiltration (10,000 m.w. membrane), producing a crude BBI concentrate. The crude concentrate is diluted with water (1:1) and again subjected to ultrafiltration (1,000 m.w. membrane) to produce a semicrude BBI concentrate which is spray dried to produce the BBIC product.

In another embodiment of the process to produce the BBIC product, the ultrafiltration step(s) are eliminated by starting with soy solubles, and applying the acetone treatment to a substrate that has a substantially higher concentration of BBI than that in defatted soy flour/flake. In this process, insolubles are removed from acid aqueous-extracted hexane defatted soybeans to produce soybean solubles having a solids content of at least 50%. The soybean solubles are diluted with water to a solids concentration of from about 15–20% and are then centrifuged to produce purified soybean solubles. Acetone is added to the supernatant to produce a crude BBI concentrate precipitate, which is allowed to settle. The resulting precipitate containing the partially purified BBI is then resuspended in water and centrifuged. Acetone is then added to the supernatant and the resulting water soluble, acetone insoluble precipitate allowed to settle, and then dried to produce the BBIC product. An optional additional acetone resuspension step can be employed before the final drying step.

It was observed that the BBIC produced in accordance with the processes described herein is highly effective at suppressing DMBA-induced oral carcinogenesis in hamsters at a concentration of 1.0%. In studies performed with the method of the present invention, it was more effective than BBI prepared by any prior art methods in the suppression of oral carcinogenesis. It has also been discovered that BBIC produced in accordance with the processes described herein is effective at an order of magnitude lower concentration than BBI produced by prior methods.

The BBIC products made in accordance with the various processes set forth herein are useful for inhibiting the malignant transformation of cells either in vivo or in vitro. The BBIC products are useful for preventing cancer or inhibiting cancer progression in an animal, such as man, by administering the compositions, either alone or in combination with a pharmaceutically acceptable carrier. Oral administration, either as a prophylactic dietary supplement or a pharmaceutical are contemplated by the teachings of the invention.

Malignant transformation as used herein refers to the process by which a normal or a "pre-malignant" cell becomes a cancer cell, that is, a "malignant" cell. The process by which a normal cell becomes a cancer cell is termed carcinogenesis.

It is well known that many agents can modify carcinogenesis in vitro and in vivo. The same agents and factors have been shown to modify carcinogenesis in animals and in vitro transformation in a comparable fashion, thus suggesting that the processes of carcinogenesis in vivo and in vitro transformation are similar. For example, Kennedy, A. R. *Mechanisms of Tumor Promotion Vol III*, T. J. Slaga, Eds , CRC Press, 1984, Chapter 2, pp 13–55, has shown that results of studies of carcinogenesis in animals to be correlated with results of transformation in vitro studies using C3H10T1/2 cells.

The in vitro transformation systems, such as the C3H10T1/2 system, utilize cells of connective tissue origin termed fibroblasts. Most human and animal cancer involves cells of epithelial origin. Transformation in vitro in fibroblasts appears to be a similar process to carcinogenesis in vivo which results in carcinomas, cancers of epithelial cell origin. Thus it is believed by those of skill in the art that the study of transformation in vitro in fibroblasts is comparable to the study of epithelial cell malignant transformation in vivo.

Research to this date has demonstrated that BBI products have been shown to suppress or inhibit chemically or radiation induced carcinogenesis or tumorigenesis in cells of both epithelial and connective tissue origin. It has been shown that BBI products suppress carcinogenesis (1) in three types of animal species: mice, rats, and hamsters; (2) in several different organ systems/tissue types: colon, lung, liver, esophagus, and cheek pouch (oral epithelium); (3) in different cell types such as those of epithelial origin (colon, liver, lung, esophagus, and cheek pouch) and connective tissue origin (fibroblasts and the cells which give rise to angiosarcomas in the liver); and (4) when given to the test animals by different routes of administration, such as i.p. or i.v. (intravenous), direct application, and dietary supplement.

The suppression or inhibition of carcinogenesis may also be indirectly monitored, by observation of levels of protease activity, oncogene expression, and/or DNA amplification. Certain types of cancer and pre-malignant cells are known to exhibit increased protease activity, that is, the increase in the concentration of at least one proteolytic enzyme, e.g., Boc-Val-Pro-Arg-MCA, Pyr-Gly-Arg-MCA, Suc-Ala-Ala-Pro-Phe-MCA (SEQ ID NO: 1), etc.; while other types of pre-malignant or cancer cells are known to exhibit aberrant oncogene expression, e.g. c-erb(B), c-fos, c-myc, BCL2, etc; and other types of pre-malignant or cancer cells are known to exhibit DNA amplification, e.g., c-myc sequences, etc. Certain embodiments of the BBIC products produced in accordance with the processes described herein contain protease inhibitory activity, and thus the degree of carcinogenesis inhibition can be monitored by studying the effects of the BBIC product upon the protease activity. It is also believed that the effects of the BBIC products for the suppression or inhibition of carcinogenesis can be monitored by studying the level of certain oncogenes. Lowering the levels of the protease activity or oncogene expression would be one method for indicating that the BBIC product administration is effectively inhibiting carcinogenesis. The effects of the BBIC products may also be monitored by observing the amounts of DNA amplification where the reduction of the gene amplification would be another method for indicating that the BBIC product administration is effectively inhibiting carcinogenesis.

The methods for inhibiting carcinogenesis using the BBIC products made in accordance with the processes set forth herein can be used in various cell systems, preferably in in vitro systems, more preferably in mammalia species, and such as humans. The carcinogenesis suppression or inhibition has been found to be effective when the carcinogenesis is chemical or radiation induced. The suppression or inhibition may not be complete, however the onset of carcinogenesis is delayed or reduced in severity in comparison to the nonuse of the BBIC products made in accordance with the present invention. The methods of the present invention are particularly preferred for inhibiting carcinogenesis afflicting the colon, esophagus, oral epithelium (e.g., squamous carcinomas), liver, lung, and bone marrow, more preferably oral epithelium.

The BBIC products made in accordance with the processes set forth herein can also be used in methods to suppress or inhibit the extension and metastasis of malignant or cancer cells. A cell system that is subjected to cancer causing agents, either of a chemical or radiation source, can be treated with an administration of the BBIC product to suppress or inhibit both the extent and severity of the malignant cells. The BBIC product can be autoclaved for greater effectiveness as an anti-metastasis agent. The autoclaving is accomplished by conventional means as described by M. Naim et al., Br. J. Nutr. 1982, 47, 281-288, which is hereby incorporated in its entirety. The protease inhibitor activity of the autoclaved BBIC product is known to be destroyed upon the autoclaving process. However, there is believed to be another anticarcinogenic agent in soybeans which survives the autoclaving process and which is capable of inhibiting the later stages of cancer cell development involving metastasis and presumably, concomitant weight loss. Therefore, BBIC and autoclaved BBIC products are also useful as anticarcinogenic agents in cancer cell progression.

An autoclaved BBIC product administered as a water gavage has been shown in a study on mice, treated with total body irradiation (TBI) to cause thymic lymphosarcoma, to decrease the mortality rate, limit the severity of the lymphosarcoma, produce greater fat stores, and produce greater overall weight gain after exposure to the radiation in comparison to a water gavage not supplemented with BBIC products. In this same study, a diet supplemented with BBIC did not have as marked a suppressive effect on the phenomena described above as did autoclaved BBIC, but did have some effect compared to control animals receiving a water gavage. In a previous study, it was observed that irradiated mice maintained on a dietary supplement containing BBIC had significantly increased weights in the latter half of the study when compared to irradiated control animals. It is believed that the increased weights in the BBIC supplemented mice resulted from the inhibition of extension and metastasis of malignant cells by BBIC. Purified BBI did not have the same effects as BBIC or autoclaved BBIC; thus, it appears that the effects observed are not due to the presence of protease inhibitor activity. Although not wishing to be bound to any theory of invention, it is believed that the BBIC/autoclaved BBIC products contain higher levels of sterols and phospholipids than purified BBI and one or both of these products are likely to be involved in the suppression of metastasis. The dose-response relationship for the effects of BBIC/autoclaved BBIC on extension and metastasis of cancer cells in unknown; it is known, however, that 0.5% wt. dietary BBIC/autoclaved BBIC is effective. As 0.5% wt. dietary BBIC is also known to be effective as a cancer preventive agent, it is believed that doses of BBIC effective as a cancer preventive agent will also be effective in the ability to prevent the extension and metastasis of malignant cells.

The administration of the BBIC products for the prevention of cancer in the methods of the present invention can be in any suitable fashion, such as enterally, parenterally, and mucosally. Preferably the administration is orally as a dietary supplement, such as a pill. The preferred concentration of the BBIC product for administration is from about 0.0001 to about 1%, preferably from about 0.001 to about 1%, more preferably from about 0.01 to about 1%, by weight of the total dietary intake, such that the amount administered is effective to suppress or inhibit carcinogenesis. Those of skill in the art will be able to determine an effective dosage level depending upon the risk of carcinogenesis to the cells of the organs being treated. For example, in mammalian species such as man, it is known that certain groups are prone to carcinogenesis, e.g., smokers, hereditary disposition, etc. The amount of the BBIC product administered can be stated in terms of the amount of chymotrypsin inhibitor (CI), which is preferably from about 10–400 CI units/day for a human of about 70 kg (150 lb), more preferably from about 10–200 CI units/day. The BBIC product can conveniently be given as a dietary supplement, such as a pill, to be taken on a daily or other time basis for a determined period of time. The BBIC product has been shown to maintain its anticarcinogenic activity while being stored at room temperature for extended periods of time.

The BBIC product can be further purified to separate out the portion of the BBIC product having only chymotrypsin inhibitory (CI) activity as described in the literature. Odeni and Ikenaka, *J. Biochem.* 1973, 74, 857. This purified CI product can be used as a more concentrated form for anticarcinogenesis treatment.

The invention is further illustrated by the following, non-limiting examples.

EXAMPLES

Example 1

139 pounds of soybean solubles from an acidic aqueous extraction of hexane-defatted soybeans was diluted to 18% solids with 332 pounds of water. The slurry of the diluted soy solubles was centrifuged to remove insoluble matter, and the partially "purified" solids were further diluted with water to a 8% solids level. These "purified" soy solubles were then subjected to ultrafiltration using a 1,000 MW cut-off membrane at 15 gpm and 105 psig, until 31 gallons of permeate was collected. The liquid containing the crude BBI concentrate was again diluted with 31 gallons of water, and the ultrafiltration step was repeated until an additional 47 gallons of permeate was collected and 45 gallons of a semi-crude BBI concentrate remained.

At this point, 55 gallons of acetone was added to 25 gallons of the concentrate; the BBI concentrate precipitate thus obtained was allowed to settle for 1 hour. The liquid supernatant was then decanted, and the precipitate containing the "purified" BBI concentrate was placed in a Buchner Funnel under vacuum to draw off the excess liquid. The dried precipitate was ground in a Waring blender and reslurried to 15% solids. The reslurried suspension was then allowed to settle and the supernatant was lyophilized. The yield was 8 pounds of product with a Chymotrypsin inhibitor (CI) level of 135.5 mgs/g.

Example 2

87.3 pounds of soybean solubles from an acidic aqueous extraction of hexane-defatted soybeans were diluted to 18% solids with 207.5 pounds of water. The slurry was centrifuged to remove the insoluble sludge material; diluted to 8% solids with water; and then subjected to ultrafiltration over a 1,000 M cutoff membrane at 15 gpm. and 100 psig. 44 pounds of permeate was collected; the crude BBI concentrate was re-diluted with 44 pounds of water, and the ultrafiltration step was repeated. 112 pounds of permeate and 163 pounds of a semi-crude BBI concentrate were collected.

270 pounds of acetone was then added to this semi-crude BBI concentrate, and the precipitated BBI concentrate thus formed was allowed to settle for 1 hour. The liquid was decanted and the precipitate was placed in a Buchner funnel under vacuum to draw off the excess liquid. It was then reslurried with water in a Waring blender, allowed to settle, and the supernatant was spray-dried. The yield was 2.3 pounds of product with a Chymotrypsin (CI) content of 261 mgs/g.

Example 3

90 pounds of soybean solubles from an acidic aqueous extraction of hexane-defatted soybeans were diluted to between 15% to 20% of solids with water. (The initial solubles contain 50–60% solids). The slurry was centrifuged to remove 3–5% of the solids, present as insoluble sludge. The supernatant solution was then diluted with water to 10% solids, and subjected to ultrafiltration over a 1,000 MW cut-off membrane. One (1) pound of high-purity water was added to this fraction containing the crude BBI concentrate for every one (1) pound of permeate that had been removed. The ultrafiltration was considered complete when the solids content had begun to decrease. At that point, the BBI concentrate was spray-dried. The yield was 14 pounds of product with a CI content of 99.2 mgs/g.

Example 4

50.2 pounds of soybean solubles from an acidic aqueous extraction of hexane-defatted soybeans was diluted to 16% of solids with 126.2 pounds of water. The slurry was centrifuged to remove 3–5% of the solids, present as insoluble sludge. The supernatant solution was then diluted with water to 10% solids, and subjected to ultrafiltration over a 10,000 MW cut-off membrane. One (1) pound of high-purity water was added to the concentrate fraction for every one (1) pound of permeate that had been removed. When the solids content had begun to decrease in the permeate, the permeate was also subjected to ultrafiltration over a 1,000 MW cut-off membrane. After that, the BBI concentrate was spray-dried. The yield was 2.6 pounds of product with a CI content of 61.9 mgs/g.

Example 5

A slurry obtained from the whey protein stream produced during the production of soy protein isolate was treated by ultra filtration over a 1,000 MW cut-off membrane, as described in Example 4. A total of 157.75 pounds of whey protein solution was used. After ultrafiltration, the BBI concentrate fraction, containing 2.7% solids, was spray-dried. The yield was 1.2 pounds of product, containing 187.8 mgs/g of CI.

Example 6

1000 gams of soy solubles with a solids content of 19% from an acidic aqueous extraction of hexane-defatted soybeans were centrifuged to remove insoluble matter. At this point, 2 liters of acetone were added to the supernatant. The crude BBI concentrate precipitate thus obtained was allowed to settle for 1 hour. The liquid supernatant was then decanted. The precipitate containing the partially purified BBI was then resuspended in 200 ml of water and centrifuged to remove matter rendered irreversibly insoluble by acetone. 400 ml of acetone was then added to the supernatant. The water soluble, acetone insoluble precipitate which was formed was allowed to settle for 1 hour. The supernatant was decanted. The major portion of water remaining in the precipitate was removed by resuspending the precipitate in 100 ml of acetone and allowing the precipitate to settle for 30 minutes. The supernatant was decanted. The BBI concentrate precipitate was spread thinly on a tray and allowed to air dry to a free flowing white powder. The yield was 5 gm of product with a chymotrypsin inhibitor level of 200 mgs/g.

Example 7

As the C3H10T1/2 cell transformation assay system was the in vitro system in which BBI was first identified as an anticarcinogenic agent, the C3H10T1/2 cell transformation assay is used for transformation studies to evaluate the anticarcinogenic activity of a composition made in accordance with the teachings of the present invention. C3H10T1/2 cells are a mouse embryo fibroblast cell line which can be transformed in culture by chemicals and radiation. When transformed, the cells pile up, forming densely staining foci against a background monolayer of contact-inhibited cells. The transformed foci are characterized as type II or type III using defined morphological criteria. A very high percentage of type II and III foci are tumorigenic when inoculated into syngeneic or nude mice.

To assay for the inhibition of oncogenic transformation by extracts of soybeans, in vitro assay, the following protocol is employed: C3H10T1/2 cells are seeded, and after 24 hours, treated with 600 R of radiation. Immediately after carcinogen treatment, the medium is changed to complete medium containing the sample of interest (at the highest nontoxic level, to at most 1 mM; we have observed in previous studies that if compounds do not have an effect at this concentration (1 mM) in the medium they will not have an effect at higher levels). Subsequently, the medium is changed at weekly intervals. The dishes are fixed and stained and the transformed foci evaluated at 6 weeks.

If a new preparation looks promising after being tested for the ability to inhibit transformation in vitro, it is tested for the ability to inhibit carcinogenesis in vivo, specifically 7,12-dimethylbenz(a) anthracene induced oral carcinogenesis in hamsters. The protocol to be utilized for these studies is the same as that described by Messadi et al., *J. Natl. Cancer Inst.* 1986, 76, 447–452.

Example 8

One hundred sixty five non-inbred male Syrian hamsters, 4 weeks old and weighing 70–90 grams, were obtained from Charles River Breeding Laboratories, Wilmington, Mass. The animals were housed 4 per cage with wood chips for bedding. The environment was controlled with an alternating 12-hour light-dark cycle. Water and Purina Laboratory Chow (#5001; Ralston Purina Co., St. Louis, Mo.) were available ad libitum. The hamsters were divided into 23 groups, 3 groups containing 4 animals each, and 20 groups containing 8 animals each (plus one extra animal in Group 17).

The 3 groups of 4 animals each were treated as follows ("0" time represents the beginning of DMBA treatments):

Group 1—1% BBI (5 times per week) for 0–180 days.

Group 2—1% PBBI (5 times per week) for 0–180 days.

Group 3—Mineral oil (3 times per week) for 0–60 days.

These groups served as controls for the other experimental groups whose treatments are described below:

Group 4—DMBA (3 times per week) for 0–60 days.

Group 5—DMBA (3 times per week) for 0–60 days+1% BBI (5 times per week) for 0–180 days.

Group 6—DMBA (3 times per week) for 0–60 days +1% BBI ("Method 8"; the invention described here) (5 times per week) for 0–180 days.

Group 7—DMBA (3 times per week) for 0–60 days +1% BBI (3 times per week) for 0–180 days.

Group 8—DMBA (3 times per week) for 0–60 days +1% BBI (one time per week) for 0–180 days.

Group 9—DMBA (3 times per week) for 0–60 days +1% BBI (5 times per week) for 0–60 days.

Group 10—DMBA (3 times per week) for 0–60 days +1% BBI (5 times per week) for 0–90 days.

Group 11—DMBA (3 times per week) for 0–60 days +1% BBI (5 times per week) for 14–90 days.

Group 12—DMBA (3 times per week) for 0–60 days +1% BBI (5 times per week) for 45–135 days.

Group 13—DMBA (3 times per week) for 0–60 days +1% BBI (5 times per week) for 90–180 days.

Group 14—DMBA (3 times per week) for 0–60 days+0.1% BBI (5 times per week) for 0–180 days.

Group 15—DMBA (3 times per week) for 0–60 days+0.01% BBI (5 times per week) for 0–180 days.

Group 16—DMBA (3 times per week) for 0–60 days+0.001% BBI (5 times per week) for 0–180 days.

Group 17—DMBA (3 times per week) for 0–60 days+1% PBBI (5 times per week) for 0–180 days.

Group 18—DMBA (3 times per week) for 0–60 days+0.1% PBBI (5 times per week) for 0–180 days.

Group 19—DMBA (3 times per week) for 0–60 days+0.01% PBBI (5 times per week) for 0–180 days.

Group 20—DMBA (3 times per week) for 0–60 days+0.001% PBBI (5 times per week) for 0–180 days.

Group 21—DMBA (3 times per week) for 0–60 days+1% PBBI (3 times per week) for 0–180 days.

Group 22—DMBA (3 times per week) for 0–60 days—+1% PBBI (1 time per week) for 0–180 days.

Group 23—DMBA (3 times per week) for 0–60 days+1% Potato Inhibitor (5 times per week) for 0–180 days.

All treatments were applied topically to the right cheek pouch as described by Salley, *J. Dent. Res.* 1954, 33, 253–262, and Morris, *J. Dent. Res.* 1961, 40, 3–15. Animals were weighed at weekly intervals. DMBA (Sigma Chemical Co., St. Louis, Mo.) was applied in a 0.25% solution in heavy mineral oil (U.S.P.) at a dose of 0.125 mg on the cheek pouch 3 times per week for 8 weeks of treatment (i.e., 0.375 mg/wk); this is a standard protocol for DMBA-induced hamster cheek pouch carcinogenesis (Salley (1954) and Morris (1961) supra).

Several preparations of protease inhibitors were used in the studies reported here. BBI is an extract of the inhibitor, "BBI concentrate," that has been described in detail elsewhere (Yavelow et al., (1985) supra) and was prepared by Central Soya (Ft. Wayne, Ind.). The extract contains five separate protease inhibitors all of which are very similar to BBI in molecular weight and trypsin inhibitory activity, Kassell, *Methods Enzymol* 1970, 19, 860–862; Hwang et al., *Biochem. Biophy. Acta.* 1977, 495,369–382. The BBI extract was dissolved in distilled water at a final concentration of 0.001–1.0%. BBI referred to as "Method 8" (MS) and prepared as described in Example 2 herein, was also supplied by Central Soya. PBBI containing BBI which has been purified to near homogeneity and is greater than 95% pure PBBI, was prepared from the BBI concentrate as previously described (Yavelow et al. (1985) supra). The potato inhibitor extract (Kemin Product No. 068129), enriched in chymotrypsin inhibitor I from potatoes (70% of the extract is the inhibitor), was prepared by Kemin Industries, Inc.

All animals were treated for 20 weeks and then sacrificed by $CO_2$ inhalation. The time between the last application of DMBA and animal sacrifices was approximately 4 months. At the time of autopsy, all organs were examined and any organs having an abnormal appearance were removed for histopathologic analysis. The location of all tumors was noted and the size in mm was recorded. The cheek pouches were carefully examined, photographed, and then prepared for histopathologic analysis. Each pouch was fixed in 10% buffered formalin and embedded in paraffin. Five-micron sections were cut and stained with hematoxylin and eosin.

For each animal of each treatment group, the results of the cheek pouch histopathologic analysis are shown in Table 1. Histopathological alterations observed in organs other than the cheek pouch are also given in Table 1. The data for the tumors of the cheek pouch (given in Table 1) are shown in histogram form in FIG. 1. Examples of hamster cheek pouches with and without tumors are shown in FIG. 2(a) and FIG. 2(b).

Figure 2A:
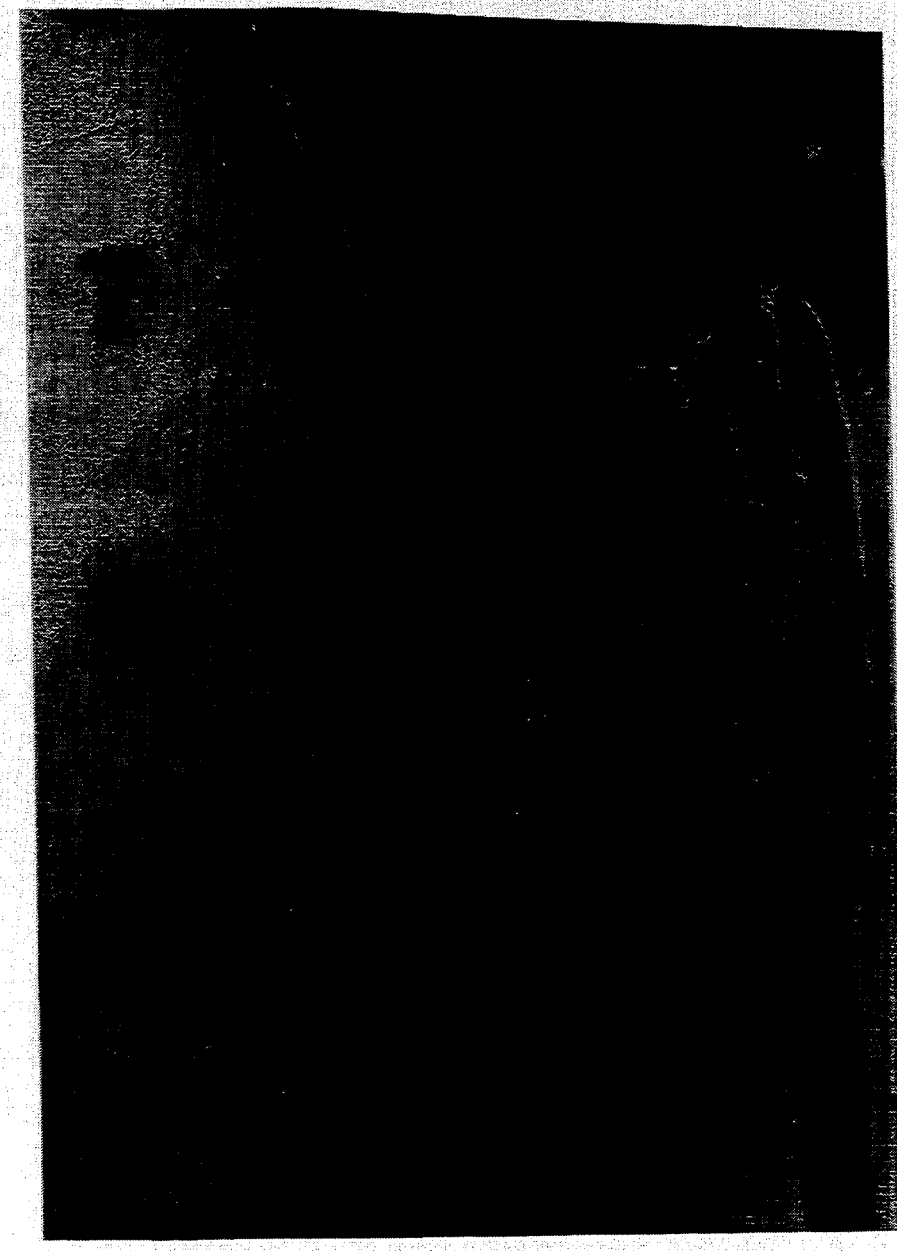
FIG. 2(a) is a photograph of a normal (untreated) hamster cheek pouch.
Figure 2B:
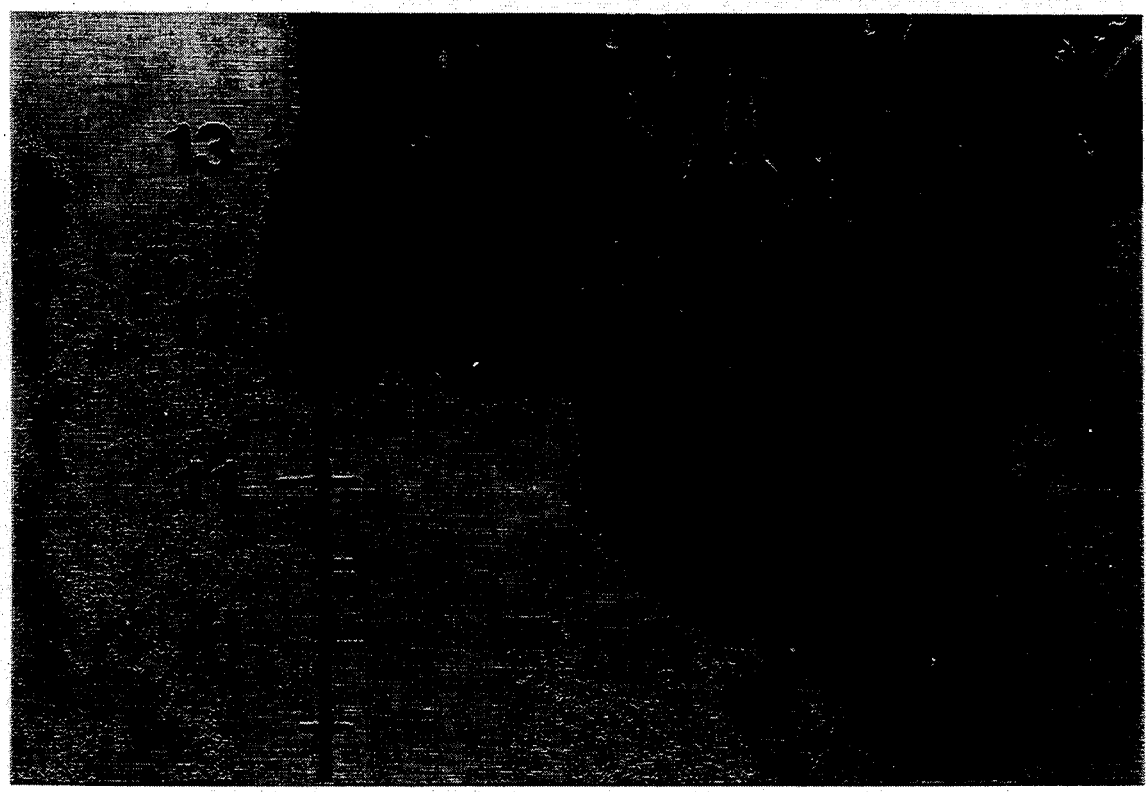
FIG. 2(b) is a photograph showing a DMBA treated hamster cheek pouch with tumors.

The conclusions that can be drawn from the data shown in Table 1 and FIG. 1 are as follows:

1) When present for the entire carcinogenesis assay period (0–180 days), BBI significantly suppresses DMBA induced oral carcinogenesis at concentrations from 1% down to 0.01% (Groups 4 vs. 5, 6, 14 and 15, $p<0.05$). At 0.001%, the suppression of carcinogenesis by BBI is not statistically significant (Group 4 rs. 16, $p>0.05$).

2) 1% BBI applications at 5 times per week, 3 times per week and once per week (for the entire carcinogenesis assay period; 0–180 days), led to a significant reduction in the DMBA induced tumor yield (Groups 4 vs. 5, 7 and 8, $p<0.05$).

3) 1% BBI applications for the following time periods led to a significantly reduced tumor yield: 0–180 days, 0–90 days, 14–90 days and 45–135 days (Groups 4 or 5, 6, 10, 11 $p<0.05$). Applications of 1% BBI from days 0–60 and 90–180 reduced the DMBA induced tumor yield, but not in a statistically significant manner (Groups 4 vs. 9, $p>0.5$; Groups 4 vs. 13, $p<0.10$).

4) The method of the invention BBI, "Method 8", gave results similar to those obtained for the previous method of preparing BBI (at 1% BBI). when applied 5 times per week for 0–180 days; both the previous method of preparing BBI and the new method ("Method 8") led to a significant reduction in the DMBA induced tumor yield (Groups 4 vs. 5, $p<0.05$; 4 vs. 6, $p<0.02$). Method 8, however, was more effective than the standard method for preparing BBI, as the results were of higher statistical significance and no malignant tumors were observed with this preparation (squamous cell carcinomas were observed in the animals treated with the standard BBI preparation).

The histopathological analysis showed that there were tumors in all of the experimental groups receiving DMBA treatments. The only DMBA+BBI groups in which no animals had malignant tumors were the groups receiving BBI prepared by the new method of the invention (specifically, group 6—Method 8), and the group receiving 0.1% BBI (group 14).

TABEL 1

Histopathologic alterations observed in the animals[1,2,3]

| Group/Treatment | Animal No. | Pigmented Lesions, Animals having | | | Tumors: Number of tumors (per animal): | | | Total tumors (per animal) | Average number of tumors/animal = Mean ± Standard Error |
|---|---|---|---|---|---|---|---|---|---|
| | | Single focus of hyperplasia | Multiple foci of hyperplasia | Papillary hyperplasia | Sebaceous gland adenomas | Papillomas | Squamous cell carcinomas (i = invasive) | | |
| 1-1% BBI | 1 | 0 | 0 | 0 | 0 | 0 | 0 | 0 | 0 |
| | 2 | 0 | 0 | 0 | 0 | 0 | 0 | 0 | |
| | 3 | 0 | 0 | 0 | 0 | 0 | 0 | 0 | |
| | 4 | 0 | 0 | 0 | 0 | 0 | 0 | 0 | |
| 2-1% PBBI | 1 | 0 | 0 | 0 | 0 | 0 | 0 | 0 | |
| | 2 | 0 | 0 | 0 | 0 | 0 | 0 | 0 | |
| | 3 | 0 | 0 | 0 | 0 | 0 | 0 | 0 | |
| | 4 | 0 | 0 | 0 | 0 | 0 | 0 | 0 | |
| 3-Mineral Oil | 1 | 0 | 0 | 0 | 0 | 0 | 0 | 0 | |
| | 2 | 0 | 0 | 0 | 0 | 0 | 0 | 0 | |
| | 3 | 0 | 0 | 0 | 0 | 0 | 0 | 0 | |
| | 4 | 0 | 0 | 0 | 0 | 0 | 0 | 0 | |
| 4-DMBA 3×/wk (0–60 d) | 1 | 0 | 0 | 0 | 0 | 1 | 5 (i) | 6 | 2.7 ± 0.9 |
| | 2 | 0 | 0 | 0 | 0 | 2 | 4 (i) | 6 | |
| | 3 | 0 | 0 | 0 | 0 | 0 | 1 (i) | 1 | |
| | 4 | x (squamous) | 0 | 0 | 0 | 0 | 0 | 0 | |
| | 5 | 0 | 0 | 0 | 0 | 0 | 1 | 1 | |
| | 6 | 0 | x | 0 | 0 | 1 | 1 (i) | 2 | |
| | 7 | 0 | 0 | 0 | 0 | 0 | 3 (i) | 3 | |
| 5-DMBA + BBI-1% 5×/wk (0–180 d) | 1 | 0 | 0 | 0 | 0 | 0 | 2 (i) | 2 | 0.6± 0.4 |
| | 2 | 0 | 0 | 0 | 0 | 1 | 0 | 1 | |
| | 3 | 0 | 0 | 0 | 0 | 2 (squamous) | 0 | 2 | |
| | 4 | 0 | 0 | 0 | 0 | 0 | 0 | 0 | |
| | 5 | 0 | 0 | 0 | 0 | 0 | 0 | 0 | |
| | 6 | 0 | 0 | 0 | 0 | 0 | 0 | 0 | |
| | 7 | 0 | 0 | 0 | 0 | 0 | 0 | 0 | |
| | 8 | 0 | 0 | 0 | 0 | 0 | 0 | 0 | |
| 6-DMBA + BBI (M8)- 1% 5×/wk (0–180 d) | 1 | 0 | x (squamous) | 0 | 0 | 0 | 0 | 0 | 0.3 ± 0.2 |
| | 2 | 0 | 0 | 0 | 0 | 1 | 0 | 1 | |
| | 3 | 0 | 0 | 0 | 1 | 0 | 0 | 1 | |
| | 4 | 0 | 0 | 0 | 0 | 0 | 0 | 0 | |
| | 5 | 0 | 0 | 0 | 0 | 0 | 0 | 0 | |

TABEL 1-continued

Histopathologic alterations observed in the animals[1,2,3]

| Group/Treatment | Animal No. | Pigmented Lesions, Animals having | | | Tumors: Number of tumors (per animal): | | | Total tumors (per animal) | Average number of tumors/animal = Mean ± Standard Error |
|---|---|---|---|---|---|---|---|---|---|
| | | Single focus of hyperplasia | Multiple foci of hyperplasia | Papillary hyperplasia | Sebaceous gland adenomas | Papillomas | Squamous cell carcinomas (i = invasive) | | |
| | 6 | 0 | 0 | 0 | 0 | 0 | 0 | 0 | |
| | 7 | 0 | 0 | 0 | 0 | 0 | 0 | 0 | |
| 7-DMBA + | 1 | 0 | x | 0 | 0 | 0 | 0 | 0 | 0.6–0.3 |
| BBI-1% | 2 | x | 0 | 0 | 0 | 0 | 0 | 0 | |
| 3×/wk | 3 | 0 | x | 0 | 0 | 0 | 1 | 1 | |
| (0–180 d) | 4 | 0 | 0 | 0 | 0 | 0 | 1 (i) | 1 | |
| | 5 | 0 | 0 | 0 | 0 | 1 | 1 | 2 | |
| | 6 | 0 | 0 | 0 | 0 | 0 | 0 | 0 | |
| | 7 | 0 | 0 | 0 | 0 | 0 | 0 | 0 | |
| 8-DMBA + | 1 | 0 | 0 | x | 0 | 1 | 1 (i) | 2 | 0.6 ± 0.3 |
| BBI-1% | 2 | 0 | 0 | 0 | 1 | 0 | 1 (i) | 2 | |
| 1×/wk | 3 | 0 | 0 | 0 | 0 | 0 | 1 | 1 | |
| (0–180 d) | 4 | 0 | 0 | 0 | 0 | 0 | 0 | 0 | |
| | 5 | 0 | 0 | 0 | 0 | 0 | 0 | 0 | |
| | 6 | 0 | 0 | 0 | 0 | 0 | 0 | 0 | |
| | 7 | 0 | 0 | 0 | 0 | 0 | 0 | 0 | |
| | 8 | 0 | 0 | 0 | 0 | 0 | 0 | 0 | |
| 9-DMBA + | 1 | 0 | 0 | x | 0 | 0 | 0 | 0 | 1.8 ± 1.8 |
| BBI-1% | 2 | 0 | 0 | x (squamous) | 0 | 0 | 0 | 0 | |
| 5×/wk | 3 | 0 | 0 | 0 | 0 | 0 | 11 (i) | 11 | |
| (0–60 d) | 4 | 0 | 0 | 0 | 0 | 0 | 0 | 0 | |
| | 5 | 0 | 0 | 0 | 0 | 0 | 0 | 0 | |
| | 6 | 0 | 0 | 0 | 0 | 0 | 0 | 0 | |
| 10-DMBA + | 1 | 0 | x | 0 | 0 | 0 | 0 | 0 | 0.3 ± 0.2 |
| BBI-1% | 2 | 0 | x | 0 | 0 | 0 | 0 | 0 | |
| 5×/wk | 3 | 0 | 0 | 0 | 0 | 0 | 1 (i) | 1 | |
| (0–90 d) | 4 | 0 | 0 | 0 | 0 | 0 | 1 | 1 | |
| | 5 | 0 | 0 | 0 | 0 | 0 | 0 | 0 | |
| | 6 | 0 | 0 | 0 | 0 | 0 | 0 | 0 | |
| | 7 | 0 | 0 | 0 | 0 | 0 | 0 | 0 | |
| 11-DMBA + | 1 | x | 0 | 0 | 0 | 0 | 1 | 1 | 0.3 ± 0.2 |
| BBI-1% | 2 | 0 | 0 | 0 | 0 | 1 | 0 | 1 | |
| 5×/wk | 3 | 0 | 0 | 0 | 0 | 0 | 0 | 0 | |
| (14–90 d) | 4 | 0 | 0 | 0 | 0 | 0 | 0 | 0 | |
| | 5 | 0 | 0 | 0 | 0 | 0 | 0 | 0 | |
| | 6 | 0 | 0 | 0 | 0 | 0 | 0 | 0 | |
| | 7 | 0 | 0 | 0 | 0 | 0 | 0 | 0 | |
| 12-DMBA + | 1 | 0 | 0 | 0 | 0 | 1 | 0 | 1 | 0.4 ± 0.2 |
| BBI-1% | 2 | 0 | 0 | 0 | 0 | 0 | 1 | 1 | |
| 5×/wk | 3 | 0 | 0 | x | 0 | 0 | 1 | 1 | |
| (45–135 d) | 4 | 0 | 0 | 0 | 0 | 0 | 0 | 0 | |
| | 5 | 0 | 0 | 0 | 0 | 0 | 0 | 0 | |
| | 6 | 0 | 0 | 0 | 0 | 0 | 0 | 0 | |
| | 7 | 0 | 0 | 0 | 0 | 0 | 0 | 0 | |
| | 8 | 0 | 0 | 0 | 0 | 0 | 0 | 0 | |
| 13-DMBA + | 1 | x | 0 | 0 | 0 | 0 | 0 | 1 | 0.7 ± 0.3 |
| BBI-1% | 2 | 0 | 0 | x | 0 | 1 | 0 | 1 | |
| 5×/wk | 3 | 0 | 0 | x (squamous) | 0 | 0 | 2 (i) | 2 | |
| (90–180 d) | 4 | 0 | 0 | 0 | 0 | 0 | 0 | 0 | |
| | 5 | 0 | 0 | 0 | 0 | 0 | 0 | 0 | |
| | 6 | 0 | 0 | 0 | 0 | 0 | 0 | 0 | |
| 14-DMBA + | 1 | 0 | 0 | 0 | 0 | 0 | 0 | 0 | 0.5 ± 0.5 |
| BBI-0.1% | 2 | x | 0 | 0 | 0 | 3 | 0 | 3 | |
| 5×/wk | 3 | 0 | 0 | x | 0 | 0 | 0 | 0 | |
| (0–180 d) | 4 | x | 0 | 0 | 0 | 0 | 0 | 0 | |
| | 5 | 0 | 0 | 0 | 0 | 0 | 0 | 0 | |
| | 6 | 0 | 0 | 0 | 0 | 0 | 0 | 0 | |
| 15-DMBA + | 1 | 0 | 0 | 0 | 0 | 1 | 0 | 1 | 0.6 ± 0.3 |
| BBI-0.01% | 2 | 0 | x | 0 | 1 | 1 | 0 | 2 | |
| 5×/wk | 3 | 0 | 0 | 0 | 0 | 0 | 0 | 0 | |
| (0–180 d) | 4 | 0 | 0 | 0 | 0 | 0 | 1 | 1 | |
| | 5 | 0 | 0 | 0 | 0 | 0 | 0 | 0 | |
| | 6 | 0 | 0 | 0 | 0 | 0 | 0 | 0 | |
| | 7 | 0 | 0 | 0 | 0 | 0 | 0 | 0 | |
| 16-DMBA + | 1 | 0 | 0 | 0 | 0 | 0 | 4 (i) | 4 | 0.9 ± 0.6 |
| BBI-0.001% | 2 | x | 0 | 0 | 0 | 0 | 0 | 0 | |
| | 3 | 0 | 0 | 0 | 1 | 0 | 0 | 1 | |
| 5×/wk | 4 | 0 | 0 | 0 | 0 | 1 | 0 | 1 | |
| (0–180 d) | 5 | 0 | 0 | 0 | 0 | 0 | 0 | 0 | |
| | 6 | 0 | 0 | 0 | 0 | 0 | 0 | 0 | |
| | 7 | 0 | 0 | 0 | 0 | 0 | 0 | 0 | |
| 17-DMBA + | 1 | 0 | 0 | x | 0 | 0 | 1 | 1 | 0.2 ± 0.2 |
| PBBA- | 2 | 0 | 0 | 0 | 0 | 0 | 0 | 0 | |

TABEL 1-continued

Histopathologic alterations observed in the animals[1,2,3]

| Group/Treatment | Animal No. | Pigmented Lesions, Animals having | | | Tumors: Number of tumors (per animal): | | | Total tumors (per animal) | Average number of tumors/animal = Mean ± Standard Error |
|---|---|---|---|---|---|---|---|---|---|
| | | Single focus of hyperplasia | Multiple foci of hyperplasia | Papillary hyperplasia | Sebaceous gland adenomas | Papillomas | Squamous cell carcinomas (i = invasive) | | |
| 1% | 3 | 0 | 0 | 0 | 0 | 0 | 1 | 1 | |
| 5×/wk | 4 | 0 | 0 | 0 | 0 | 0 | 0 | 0 | |
| (0–180 d) | 5 | 0 | 0 | 0 | 0 | 0 | 0 | 0 | |
| | 6 | 0 | 0 | 0 | 0 | 0 | 0 | 0 | |
| | 7 | 0 | 0 | 0 | 0 | 0 | 0 | 0 | |
| | 8 | 0 | 0 | 0 | 0 | 0 | 0 | 0 | |
| | 9 | 0 | 0 | 0 | 0 | 0 | 0 | 0 | |
| 18-DMBA + | 1 | x | 0 | 0 | 0 | 0 | 0 | 0 | 0.5 ± 0.5 |
| PBBI- | 2 | x (squamous) | 0 | 0 | 0 | 0 | 0 | 0 | |
| 0.1% | 3 | 0 | x | 0 | 0 | 0 | 3 (i) | 0 | |
| 5×/wk | 4 | 0 | 0 | 0 | 0 | 0 | 0 | 4 | |
| (0–180 d) | 5 | 0 | x | 0 | 0 | 0 | 0 | 0 | |
| | 6 | 0 | 0 | 0 | 0 | 0 | 0 | 0 | |
| | 7 | 0 | 0 | 0 | 0 | 0 | 0 | 0 | |
| | 8 | 0 | 0 | 0 | 0 | 0 | 0 | 0 | |
| 19-DMBA + | 1 | 0 | 0 | 0 | 0 | 0 | 3-papillary (i) | 3 | 0.3 ± 0.2 |
| PBBI- | 2 | 0 | 0 | 0 | 0 | 0 | 0 | 0 | |
| 0.01% | 3 | 0 | 0 | 0 | 0 | 0 | 0 | 0 | |
| 5×/wk | 4 | 0 | 0 | 0 | 0 | 0 | 0 | 0 | |
| (0–180 d) | 5 | 0 | 0 | 0 | 0 | 0 | 0 | 0 | |
| | 6 | 0 | 0 | 0 | 0 | 0 | 1 (i) | 1 | |
| | 7 | 0 | 0 | 0 | 0 | 0 | 0 | 0 | |
| 20-DMBA + | 1 | 0 | x | 0 | 0 | 0 | 0 | 0 | 1.6 ± 1.0 |
| PBBI- | 2 | 0 | 0 | 0 | 0 | 0 | 6 (i) | 6 | |
| 0.001% | 3 | 0 | x | 0 | 0 | 2 | 3 (i) | 5 | |
| 5×/wk | 4 | 0 | 0 | 0 | 0 | 0 | 0 | 0 | |
| (0–180 d) | 5 | 0 | 0 | 0 | 0 | 0 | 0 | 0 | |
| | 6 | 0 | 0 | 0 | 0 | 0 | 0 | 0 | |
| | 7 | 0 | 0 | 0 | 0 | 0 | 0 | 0 | |
| 21-DMBA + | 1 | 0 | x | 0 | 0 | 0 | 0 | 0 | 0.6 ± 0.4 |
| PBBI- | 2 | 0 | 0 | 0 | 1 | 0 | 1 | 2 | |
| 1% | 3 | 0 | 0 | 0 | 1 | 0 | 1 | 2 | |
| 3×/wk | 4 | 0 | 0 | 0 | 0 | 0 | 0 | 0 | |
| (0–180 d) | 5 | 0 | 0 | 0 | 0 | 0 | 0 | 0 | |
| | 6 | 0 | 0 | 0 | 0 | 0 | 0 | 0 | |
| | 7 | 0 | 0 | 0 | 0 | 0 | 0 | 0 | |
| 22-DMBA + | 1 | x | 0 | 0 | 0 | 1 | 1 | 2 | 0.5 ± 0.3 |
| PBBI- | 2 | 0 | 0 | x | 0 | 0 | 0 | 0 | |
| 1% | 3 | 0 | 0 | 0 | 0 | 1 | 0 | 1 | |
| 1×/wk | 4 | 0 | 0 | 0 | 0 | 0 | 0 | 0 | |
| (0–180 d) | 5 | 0 | 0 | 0 | 0 | 0 | 0 | 0 | |
| | 6 | 0 | 0 | 0 | 0 | 0 | 0 | 0 | |
| 23-DMBA + | 1 | 0 | 0 | 0 | 0 | 1 | 1 (i) | 2 | 1.4 ± 0.3 |
| Pot. Inh.- | 2 | 0 | 0 | 0 | 1 | 0 | 1 | 2 | |
| 1% | 3 | 0 | 0 | 0 | 0 | 0 | 1 | 1 | |
| 5×/wk | 4 | 0 | 0 | 0 | 0 | 0 | 1 | 1 | |
| (0–180 d) | 5 | 0 | 0 | 0 | 0 | 0 | 1 (i) | 1 | |

Footnotes
1. Abbreviations used:
BBI = BBI concentrate; PBBI Pure BBI
2. Other Pathology Observed in the Various Treatment Groups:
Group 4, animal 2 = Hyperplastic spleen
Group 9, animal 3 = Hyperplastic spleen
Group 12, animal 5 = Kidney nephrosis
Group 14, animal 1 = Stomach, squamous papillary hyperplasia
Group 16, animal 4 = Melanin nodule
Group 18, animal 6 = Leukemic node
Group 21, animal 7 = Stomach papillomas; lymphoreticular tumor
3. Statistical Analysis (Student's t-test):
Groups 4 vs. 5, $p < 0.05$; 4 vs. 6, $p < 0.02$; 4 vs. 7, $p < 0.05$; 4 vs. 8, $p < 0.05$; 4 vs. 9, $p > 0.05$; 4 vs. 10, $p < 0.02$; 4 vs. 11, $p < 0.02$; 4 vs. 12, $p < 0.05$; 4 vs. 13, $p < 0.10$; 4 vs. 14, $p < 0.05$; 4 vs. 15, $p < 0.05$; 4 vs. 16, $p > 0.05$; 4 vs. 17, $p < 0.01$; 4 vs. 18, $p < 0.05$; 4 vs. 19, $p < 0.02$; 4 vs. 20, $p > 0.05$; 4 vs. 21, $p < 0.05$; 4 vs. 22, $p < 0.05$; 4 vs. 23, $p > 0.05$.

Example 9

Autoclaved BBI concentrate products were investigated for their ability to protect against metastasis of radiation-induced thymic lymphosarcoma and weight loss in mice.

Fifty-five male seven-week old C57B1/6 mice were randomly segregated into 11 study groups and housed one or two animals per cage. The mice were given acidified water and standard mouse chow (Purina) ad libitum and gavaged five days per week with food additives, shown in Table 2, dissolved in one milliliter distilled water. The food additives were purified BBI, BBI concentrate, and autoclaved BBI concentrate. The BBI concentrate (BBIC) was prepared by Central Soya. The purified BBI was prepared by the methods described by Yavelow et al., *Proc. Natl. Acad. Sci. USA* 1985, 82, 5395–99. The irradiation procedures are those described by Berenblum et al., *Radiat. Res.* 1974, 60, 501–505. The autoclaved BBI concentrate was prepared by autoclaving the BBI concentrate. The autoclaved BBI concentrate had all protease inhibitor activity destroyed by the heat treatment. The anticarcinogenic activity of BBI concentrate is thought to be due to the chymotrypsin inhibitor activity; the chymotrypsin inhibitor activity of the BBI concentrate used in this study was 100 mg/g. Purified BBI was dosed at approximately 0.1% of the diet (49 mg purified BBI/week/mouse); BBI concentrate and autoclaved BBI concentrate were dosed at a level equivalent to approximately 0.5% of the diet (245 mg. BBI concentrate or autoclaved BBI concentrate/week/mouse). Weekly weight gain and daily food intake were monitored.

TABLE 2

1. No treatment
2. Sham TBI/water
3. 0.5% BBIC (245 mg BBIC/week/mouse)
4. 0.5% autoclaved BBIC (245 mg autoclaved BBIC/week/mouse)
5. 0.1% purified BBI (49 mg purified BBI/week/mouse)
6. TBI/water
7. TBI/0.1% purified BBI (49 mg purified BBI/week/mouse)
8. TBI/0.5% BBIC (245 mg BBIC/week/mouse)
9. TBI/0.5% autoclaved BBIC (245 mg autoclaved BBIC/week/mouse)

Following seven days of gavage, test groups 6–9 were subject to total body irradiation (TBI) while they were awake in an orthovoltage unit operated at 240 kVp with 1.7 Gy weekly for four weeks. The test groups 1–5 were not given an irradiation treatment. During and after the irradiation period of four weeks, the food additives were given by gavage 5 days per week. At the end of the study, all animals were sacrificed and the tissues prepared for histopathological examination.

Subjective evaluation of falciform, mesenteric and subcutaneous fat stores were performed by two independent evaluators. For each location, normal fat stores were graded +1 with a continuum to no fat stores, graded 0. Total fat stores in each mouse was the sum of the grades of each of the three areas. Final total fat stores ranged from 3.0 to 0.

Lymphosarcoma was graded histopathologically based upon severity, as follows:

0.0—no evidence of lymphosarcoma;
1.0—thymic regeneration;
1.5—thymic dysplasia/early lymphosarcoma;
2.0—lymphosarcoma limited to thymus;
3.0—extension into lungs and/or heart;
4.0—lymphosarcoma metastasis to liver, kidneys and/or lymph nodes.

A summary of the data of the study is shown in Table 3. The mice in groups 1–5, which did not receive the irradiation treatment, showed no signs of lymphosarcoma. The mice in groups 6–9, which were subject to TBI, all showed signs of lymphosarcoma. The mice that were given the food supplement containing the autoclaved BBI concentrate had a significantly lower frequency rate of death, higher average body fat, higher average final weight gain, lower percentage lymphosarcoma, and a lower average grade lymphosarcoma.

TABLE 3

Summary of Data for C57Bl/6 Mice Treated With Different Forms of Bowman-Birk Inhibitor With or Without Total-Body Radiation Therapy

| Group | Number | Deaths[a] | Average Body fat[b] | Average Final Weight Gain[c] (SE) | Lymphosarcoma (%) | Average Grade Lymphosarcoma[d] |
|---|---|---|---|---|---|---|
| (1) No Treatment | 5 | 0 | 3 | 22.8 (1.7) | 0 | 0 |
| (2) SHAM TBI $H_2O$ | 5 | 0 | 2.6 | 21.6 (2.1) | 0 | 0 |
| (3) BBI concentrate | 11 | 0 | 2.4 | 22.1 (1.1) | 0 | 0 |
| (4) Autoclaved BBI concentrate | 4 | 0 | 2.6 | 23.6 (2.1) | 0 | 0 |
| (5) Purified BBI | 5 | 0 | 2.6 | 22.3 (1.5) | 0 | 0 |
| (6) TBI/$H_2O$ | 5 | 3/5 (60%) | 1.3 | 14.3 (2.2) | 5/5 (100) | 3.3 |
| (7) TBI/purified BBI | 5 | 3/5 (60%) | 1.2 | 12.6 (4.7) | 4/5 (90) | 4.0 |
| (8) TBI/BBI concentrate | 10 | 3/10 (33%) | 2.1 | 16.1 (2.5) | 8/9[e] (89) | 3.0 |
| (9) TBI/autoclaved BBI concentrate | 5 | 0/5 (0%) | 3.0 | 25.2 (1.1) | 3/5 (60) | 0.9 |

[a] Mice that died before euthanasia at 6 months postirradiation. Statistical analysis ($X_2$): Groups TBI/$H_2O$ vs TBI autoclaved BBI concentrate, $p < 0.05$.
[b] Statistical analysis (Student's test): Groups TBI/$H_2O$ vs TBI autoclaved BBI concentrate, TBI/$H_2O$ vs sham $H_2O$, $p < 0.05$.
[c] Statistical analysis (Student's test): Groups TBI/$H_2O$ vs TBI autoclaved BBI concentrate, TBI/$H_2O$ vs sham $H_2O$, $p < 0.05$.
[d] Statistical analysis (Student's test): Groups TBI/$H_2O$ vs TBI autoclaved BBI concentrate, TBI/$H_2O$ vs sham $H_2O$, $p < 0.05$.
[e] Complete autopsy not available on one mouse.

Example 10

A comparison study was conducted to demonstrate the effect of the BBI concentrate (BBIC) produced by methods of the present invention as compared to the BBIC produced by the method shown in U.S. Pat. No. 4,793,996, to Kennedy.

Different preparations of BBIC were received from Central Soya (Fort Wayne, Ind.). The BBIC was prepared by three different processes. The method A BBIC was prepared in accordance to the procedures set forth in the Example of U.S. Pat. No. 4,793,996 using acetone in the defatting step. The method B BBIC was prepared in accordance with Example 1 of the present invention and the method C BBIC was prepared in accordance with Example 2 of the present invention. The BBIC was dissolved with distilled water to concentration levels of 0.001–1%.

Non-inbred male Syrian hamsters, four-weeks old and weighing 70–90 grams, were obtained from Charles Breeding Laboratories. The animals were housed four per cage with wood chips for bedding. The environment was controlled with an alternating twelve hour light/dark cycle.

DMBA from Sigma Chemical Company, St. Louis, Mo., was applied in a 0.25% solution in heavy mineral oil (USP) at a dose of 0.125 mg on each cheek pouch three times per week for eight weeks of treatment (0.75 mg/wk). All treatments were applied topically to both cheek pouches.

The BBIC solutions were applied to both cheek pouches five times per week, excluding weekends. The control group, group 1, received an equal volume of water applied to the cheek pouches.

The animals were treated with the BBIC preparations for 20 weeks and then sacrificed by $CO_2$ inhalation. At the time of autopsy, all organs were examined and any organs having an abnormal appearance were removed for histopathologic analysis. The cheek pouches were carefully examined, the tumors were counted, and their location noted and their size recorded. The cheek pouches were prepared for histopathologic analysis. Each pouch was fixed in 10% buffered formalin and embedded in paraffin. Five micron sections were cut and stained with hematoxylin and eosin.

The results of the experiment are set forth in Table 4. The histopathologic analysis indicated that all tumors were squamous carcinomas. The BBIC product produced in accordance with the methods of the present invention was shown to reduce the number of tumors found in each hamster as compared to the BBIC product made in accordance with the example set forth in U.S. Pat. No. 4,793,996. The statistical analysis of the results, student's T-test, is as follows:

Groups 1 v. 2—$p<0.05$;
Groups 1 v. 3—$p<0.05$;
Groups 1 v. 4—$p>0.05$;
Groups 1 v. 5, 6, 7, 8, 9 or 10—$p<0.01$.

TABLE 4

| Treatment | Group 1 DMBA | Group 2 DMBA + 1% Method A | Group 3 DMBA + 0.01% Method A | Group 4 DMBA + 0.001% Method A | Group 5 DMBA + 1% Method B | Group 6 DMBA + 0.01% Method B |
|---|---|---|---|---|---|---|
| Total | 16 | 4 | 16 | 10 | 8 | 10 |
| Number | 17 | 17 | 17 | 19 | 14 | 9 |
| of | 19 | 13 | 14 | 23 | 12 | 11 |
| Cheek | 20 | 10 | 23 | 16 | 2 | 7 |
| Pouch | 15 | 10 | 4 | 18 | 6 | 10 |
| Tumors | 18 | 18 | 17 | 14 | 11 | 1 |
| in Each | 22 | 4 | 4 | 13 | 8 | 3 |
| Hamster | 22 | 6 | 6 | 17 | 6 | 3 |
| Mean ± S.E. | 18.6 ± 0.9 | 9.8 ± 2.3 | 12.6 ± 2.5 | 16.3 ± 1.4 | 8.4 ± 1.4 | 6.8 ± 1.4 |

| Treatment | Group 7 DMBA + 0.001% Method B | Group 8 DMBA + 1% Method C | Group 9 DMBA + 0.001% Method C | Group 10 DMBA + 0.001% Method C |
|---|---|---|---|---|
| Total | 7 | 1 | 0 | 6 |
| Number | 14 | 4 | 4 | 10 |
| of | 15 | 3 | 0 | 4 |
| Cheek | 8 | 4 | 12 | 3 |
| Pouch | 4 | 2 | 7 | 9 |
| Tumors | 8 | 5 | 9 | 8 |
| in Each | 3 | 10 | 9 | 6 |
| Hamster | 0 | 10 | 7 | 10 |
| Mean ± S.E. | 7.4 ± 1.9 | 4.9 ± 1.2 | 6.0 ± 1.5 | 7.0 ± 1.0 |

What is claimed is:

1. A method for inhibiting carcinogenesis in an animal which is susceptible to cancer comprising:
 (a) providing a Bowman-Birk inhibitor product produced by the steps consisting essentially of:
  (i) providing soybean solubles produced from acidic aqueous-extracted hexane-defatted soybeans;
  (ii) diluting the soybean solubles with an aqueous solution to form a slurry;
  (iii) separating the aqueous soluble portion of the soybean solubles from the slurry to form a purified soybean soluble composition;
  (iv) diluting the purified soybean soluble composition with an aqueous solution and ultrafiltering the aqueous soluble portion of the diluted purified soybean soluble composition at least once to form a crude Bowman-Birk inhibitor concentrate; and
  (v) drying the crude Bowman-Birk inhibitor concentrate and recovering a Bowman-Birk inhibitor concentrate product; and
 (b) administering the Bowman-Birk inhibitor concentrate product to an animal which is susceptible to cancer in an amount effective to inhibit carcinogenesis.

2. The method of claim 1 wherein the drying step is spray drying.

3. The method of claim 2 wherein the slurry of step (a)(ii) is a 15 to 20 percent solid solution.

4. The method of claim 1 further comprising autoclaving the Bowman-Birk inhibitor concentrate product.

5. The method of claim 4 wherein the drying step is spray drying.

6. The method of claim 2 further comprising diluting the crude Bowman-Birk inhibitor concentrate with an aqueous solution and separating a semi-crude Bowman-Birk inhibitor concentrate prior to the spray drying.

7. The method of claim 6 further comprising, prior to the drying step, diluting the semi-crude Bowman-Birk inhibitor concentrate with acetone and retaining the precipitated acetone insoluble portion.

8. The method of claim 7 further comprising lyophilizing the dried Bowman-Birk inhibitor product.

9. The method of claim 7 further comprising autoclaving the dried Bowman-Birk inhibitor product.

10. The methods of claims 1, 4, 7 or 9 wherein the administration is to a human and is oral.

11. The methods of claims 1, 4, 7 or 9 wherein the administration comprises from about 0.0001 to 1 percent by weight of the dietary intake of the human.

12. A method for inhibiting carcinogenesis in an animal which is susceptible to cancer comprising:
   (a) providing a Bowman-Birk inhibitor product produced by the steps consisting essentially of:
      (i) providing soybean solubles produced from acidic aqueous-extracted hexane-defatted soybeans;
      (ii) diluting the soybean solubles with an aqueous solution to form a slurry;
      (iii) separating the aqueous soluble portion of the soybean solubles from the slurry to form a purified soybean soluble composition;
      (iv) diluting the first concentrate with water and separating a second aqueous soybean soluble portion;
      (v) adding acetone to the second aqueous portion to produce a second Bowman-Birk inhibitor precipitate concentrate;
      (vi) drying the second Bowman-Birk concentrate and to produce a Bowman-Birk concentrate product; and
   (b) administering the Bowman-Birk inhibitor product to an animal which is susceptible to cancer in an amount effective to inhibit carcinogenesis.

13. The method of claim 12 wherein the drying step is spray drying.

14. The method of claim 13 further comprising adding acetone to the second Bowman-Birk concentrate prior to the drying step.

15. The method of claim 14 further comprising lyophilizing the dried Bowman-Birk concentrate product.

16. The method of claim 12 further comprising autoclaving the dried Bowman-Birk concentrate product.

17. The methods of claims 12, 14 or 16 wherein the administration is to a human and is oral.

18. The methods of claims 12, 14, or 16 wherein the administration comprises from about 0.0001 to 1 percent of the dietary intake of the human.

* * * * *